(12) United States Patent
Richardson et al.

(10) Patent No.: US 10,499,828 B2
(45) Date of Patent: Dec. 10, 2019

(54) SYSTEM AND METHOD FOR HEART MONITORING

(75) Inventors: Charles L. Richardson, Monroe, NC (US); Michael L. Smith, Matthews, NC (US); Franz W. Kellar, Gastonia, NC (US)

(73) Assignee: Lifescience Solutions, LLC, Charlotte, NC (US)

( * ) Notice: Subject to any disclaimer, the term of this patent is extended or adjusted under 35 U.S.C. 154(b) by 992 days.

(21) Appl. No.: 11/738,962

(22) Filed: Apr. 23, 2007

(65) Prior Publication Data

US 2007/0191722 A1 Aug. 16, 2007
US 2013/0012826 A9 Jan. 10, 2013

Related U.S. Application Data

(63) Continuation-in-part of application No. 11/072,463, filed on Mar. 7, 2005, now Pat. No. 7,917,195.

(60) Provisional application No. 60/550,533, filed on Mar. 5, 2004.

(51) Int. Cl.
| | |
|---|---|
| *A61B 5/04* | (2006.01) |
| *A61B 5/0452* | (2006.01) |
| *A61N 1/372* | (2006.01) |
| *A61B 5/00* | (2006.01) |
| *A61N 1/37* | (2006.01) |

(52) U.S. Cl.
CPC .......... *A61B 5/04525* (2013.01); *A61B 5/413* (2013.01); *A61N 1/37211* (2013.01); *A61B 5/0006* (2013.01); *A61N 1/3702* (2013.01); *A61N 1/37247* (2013.01); *A61N 1/37282* (2013.01)

(58) Field of Classification Search
USPC .................. 600/509–510, 513, 523, 546; 607/115–116, 118
See application file for complete search history.

(56) References Cited

U.S. PATENT DOCUMENTS

| | | |
|---|---|---|
| 3,302,639 A | 2/1967 | Koffler |
| 3,523,539 A | 8/1970 | Lavezzo et al. |
| 3,662,758 A | 5/1972 | Glover |

(Continued)

FOREIGN PATENT DOCUMENTS

| | | |
|---|---|---|
| WO | WO 00/40148 A1 | 7/2000 |
| WO | WO 2008/029362 A1 | 3/2008 |

OTHER PUBLICATIONS

Office Action for Chinese Application No. 2008800215701 issued Feb. 11, 2011.

*Primary Examiner* — Deborah Malamud
(74) *Attorney, Agent, or Firm* — Waller Lansden Dortch & Davis, LLP; Matthew C. Cox

(57) ABSTRACT

The present invention provides systems and methods for monitoring a heart. According to one embodiment, the system includes an implantable registering unit for registering an electrical signal from the heart. The system includes a local data unit in operable communication with registering unit. The local data unit may be placed in communication with a computer, which may be at a location remote from the local data unit. The computer is adapted to receive the data from the local data unit corresponding to the registered electrical signal and to compare the registered electrical signal to a reference electrical signal to determine whether the heart is functioning properly.

15 Claims, 12 Drawing Sheets

(56) References Cited

U.S. PATENT DOCUMENTS

| | | |
|---|---|---|
| 3,669,120 A | 6/1972 | Nielsen |
| 3,835,865 A | 9/1974 | Bowers |
| 3,925,041 A | 12/1975 | Patterson et al. |
| 3,985,142 A | 10/1976 | Wickham |
| 4,114,627 A | 9/1978 | Lewyn et al. |
| 4,492,235 A | 1/1985 | Sitrick |
| 4,531,527 A | 7/1985 | Reinhold, Jr. et al. |
| 4,821,724 A | 4/1989 | Whigham et al. |
| 5,090,418 A | 2/1992 | Squires et al. |
| 5,092,343 A | 3/1992 | Spitzer et al. |
| 5,139,028 A | 8/1992 | Steinhaus et al. |
| 5,139,668 A | 8/1992 | Pan et al. |
| 5,161,540 A | 11/1992 | Mueller |
| 5,197,480 A | 3/1993 | Gebhardt |
| 5,246,008 A | 9/1993 | Mueller |
| 5,411,031 A | 5/1995 | Yomtov |
| 5,782,890 A | 7/1998 | Wahlstrand et al. |
| 5,820,659 A | 10/1998 | Ekiner et al. |
| 5,833,623 A | 11/1998 | Mann et al. |
| 6,044,294 A | 3/2000 | Mortazavi et al. |
| 6,152,882 A * | 11/2000 | Prutchi .................... 600/509 |
| 6,198,965 B1 | 3/2001 | Penner et al. |
| 6,234,973 B1 | 5/2001 | Meador et al. |
| 6,269,264 B1 | 7/2001 | Weyant et al. |
| 6,411,840 B1 | 6/2002 | Bardy |
| 6,424,860 B1 | 7/2002 | Karlsson |
| 6,473,638 B2 | 10/2002 | Ferek-Petric |
| 6,740,636 B2 | 5/2004 | Horuk |
| 6,745,076 B2 | 6/2004 | Wohlgemuth et al. |
| 6,824,592 B2 | 11/2004 | Monzyk et al. |
| 6,983,183 B2 | 1/2006 | Thiagarajan et al. |
| 7,277,754 B2 | 10/2007 | McCabe et al. |
| 2002/0198445 A1 | 12/2002 | Dominguez et al. |
| 2003/0158466 A1 | 8/2003 | Lynn et al. |
| 2003/0163057 A1 | 8/2003 | Flick et al. |
| 2005/0027323 A1 | 2/2005 | Mulligan et al. |
| 2005/0049474 A1 | 3/2005 | Kellogg et al. |
| 2005/0113703 A1 | 5/2005 | Farringdon et al. |
| 2005/0234360 A1 | 10/2005 | Richardson |
| 2007/0062870 A1 | 3/2007 | Chen et al. |
| 2007/0156030 A1 | 7/2007 | Richardson |
| 2007/0179392 A1 | 8/2007 | Zhang |
| 2007/0191722 A1 | 8/2007 | Richardson |

* cited by examiner

—— ORIGINAL TEMPLATE
—·· FOLLOW UP TEMPLATE
⫽ AREA OF DISCREPANCY
(FOR COMPARISON OF % MATCH)

— ORIGINAL TEMPLATE
--- FOLLOW UP TEMPLATE
⫽ POINT COMPARISON MODEL
(FOR COMPARISON OF % MATCH)

| BIOPSY GRADE | SCALE OF REJECTION |
|---|---|
|  | 0 |
| 0 | 1 |
| 1A | 2 |
| 1B | 3 |
| 2 | 4 |
| 3A | 5 |
| 3B | 6 |
| 4 | 7 |

FIG. 18

SYSTEM AND METHOD FOR HEART MONITORING

CROSS-REFERENCE TO RELATED APPLICATIONS

This application is a Continuation-In-Part of U.S. patent application Ser. No. 11/072,463, filed Mar. 7, 2005 now U.S. Pat. No. 7,917,195, which claims the benefit of U.S. Provisional Application No. 60/550,533, filed Mar. 5, 2004.

BACKGROUND OF THE INVENTION

The present invention relates generally to medical apparatus and methods for monitoring and evaluating cardiac function and, more particularly, to non-invasive apparatus and methods for monitoring and evaluating the cardiac function of heart transplant and congestive heart failure patients, detecting heart failure in such patients and providing an appropriate warning to the patient and/or physician in the event of actual or anticipated heart failure, and/or administering therapeutic drugs to the patient to treat the patient's condition.

Cardiovascular disease if the leading cause of death for both men and women in the U.S. today and claims more lives each year than the next five leading causes of death combined.

In the United States, nearly 5 million patients have been diagnosed with heart failure. Each year more than 500,000 new cases are recognized. This represents, by far the fastest growing area of cardiology. As many as 20% of these patients qualify for an implanted device, either an implantable pacemaker or implantable cardiac defibrillator ("ICD") or a biventricular pacemaker/ICD, and a fortunate percent of those severely symptomatic individuals will go on to cardiac transplant.

The primary diagnoses associated with heart transplantation are coronary artery disease (45%) and cardiomyopathy (45%), with congenital heart disease accounting for 8% and approximately 3% for retransplantation.

Each year approximately 2,500 cardiac transplants are performed in the United States and this number approaches 5,000 worldwide. One-year survival is approximately 85% in experienced transplant centers, with a five-year survival rate approaching approximately 70%. The most common cause of death is infection, followed by acute rejection. Although technology exists to treat bradycardia and tachycardia, i.e., pacemakers and defibrillators, respectively, the currently available apparatus and methods for monitoring a transplanted heart or for assisting in congestive heart failure assessment are quite limited and, for the most part, require the patient to undergo extensive invasive procedures or repetitive visits to a hospital or other medical facility which can be expensive.

Known methods for monitoring patients who receive a heart transplant generally involve an invasive procedure called endomyocardial biopsy ("EMB"). EMB procedures typically require an invasive biopsy of the transplanted heart in which the patient is taken to a catheterization laboratory and a large blood vessel (usually in the neck) is cannulated allowing a biopsy catheter to be advanced into the right side of the heart. Several small pieces or bites of the myocardium are sampled during the EMB, which are then sent for pathological evaluation. Similar invasive procedures are required of patients suffering from congestive heart failure, including catheterization to evaluate pressures inside the heart.

As discussed above, the rejection of a transplanted heart by the patient's body is one of the leading causes of death during the first year following the transplant. In order to detect early rejection of a transplanted heart, multiple EMBs are performed at regular, predetermined intervals. The typical patient undergoes up to twenty (20) EMBs during the first year. After the first year, even patients who have not experienced a rejection episode continue to require periodic EMBs to insure normal function of the transplanted heart. Although EMBs detect rejection and allow treatment in order to prevent death of the transplant patient, EMBs themselves result in a substantial risk of bleeding, infection, cardiac perforation, and other morbidities including death. In addition, this catheterization procedure is not only costly, but also painful and inconvenient for the patient.

Medical practitioners have attempted to reduce the risks associated with EMBs by exploring alternative methods for predicting transplant rejection and/or complications from congestive heart failure. For example, during the last decade investigators in Europe focused on intramyocardial electrograms and immune system markers that had the potential for predicting ischemia as well as acute transplant rejection. In studies on canines evaluating data from four myocardial sites, it was found that analysis of the mean intramyocardial unipolar peak-to-peak R-wave amplitude had a sensitivity (i.e., an ability to identify rejection) and a specificity (i.e., percentage of false positives) sufficient for diagnosing most transplant rejection. It also was discovered that, as the number of myocardial leads increases (i.e., the number of myocardial sites monitored increases), the sensitivity of detecting transplant rejection also increased. Preliminary studies on humans were able to show a correlation between acute rejection episodes and the mean amplitude of the R-wave of the QRS complex.

Over the past fifteen years, more than one thousand prototype unipolar, peak-to-peak rejection monitors ("UPPRMs") have been implanted in both adults and children. UPPRMs require two or more electrodes attached to the patient's heart that are structured to register QRS voltage. The amplitude measurement of the intramyocardial electrogram ("IMEG") was used to predict rejection.

Another method of conventional rejection monitoring is disclosed in U.S. Pat. No. 5,246,008 to Mueller, which is incorporated herein. As disclosed in Mueller, the rejection monitor ("RM") or telemetry measuring unit preferably is connected to the patient's heart using two pairs of current and measuring electrodes in which each current electrode is annularly surrounded by a measuring electrode. This RM includes a miniaturized, battery-operated electronic measuring circuit for impedance measurement. The RM also has a transmitter-receiver circuit for electromagnetic waves with a carrier frequency of one coil being able to function as the antenna. An AC voltage is applied in a square-wave pulse to the tissue via the current electrodes. The impedance of the body tissue is then measured via the measuring electrodes. The receiver coil of a telemetry control unit can be disposed on the body of the patient over the RM, preferably during the night rest periods. The control unit transmits an ON signal via the receiver coil to the RM via the antenna. The RM then begins applying AC voltage in a square-wave pulse utilizing the current electrodes and measuring the impedance via the measuring electrodes. The RM transmits the measured values for a predetermined measuring duration via the induction coupling formed by the antenna and receiver coil to the control unit. The measured values are stored by the control unit, such as on a computer, and values can be called in by a clinic using a modem via a telephone line.

As disclosed in Mueller, the impedance consists substantially of the ohmic resistance and a capacitive reactance. The ohmic resistance depends substantially on the extracellular space of the tissue, whereas the capacitive reactance depends substantially on the properties of the cell membrane. As a result of ischemia of the tissue during a rejection reaction, intracellular edema with simultaneous shrinkage of the extracellular space occurs, which results in changes to the ohmic resistance and capacitive reactance of the tissue. The change of the pulse form of the ac voltage is a measure of the impedance. If a square-pulse voltage is used as the ac voltage, the change of the pulse height corresponds to the ohmic resistance, whereas the change in the steepness of the leading edges of the square-wave pulses is a measure of the capacitive reactance.

Results have suggested several advantages of these alternative methods over current methods of transplant rejection assessment such as EMBs. In particular, UPPRMs enabled reliable recognition of transplant rejection episodes at an early stage, thus allowing prompt treatment to reverse rejection and to block further development to more severe stages. Because advanced stages of transplant rejection were not encountered, the amount of additional immuno-suppression necessary to terminate rejection was moderate thereby reducing the treatment costs. Compared to an eighty-five percent (85%) survival rate for one-year post transplant when EMBs are used to assess transplant rejection, there were no deaths from acute transplant rejection when UPPRMs was used to assess rejection, provided the patient adhered strictly to short-interval, and preferably daily, IMEG recording. Biopsy findings showed the IMEGs to have one hundred percent (100%) sensitivity and ninety-seven percent (97%) specificity in detecting transplant rejection and there were 3% false negatives. In those few cases when the UPPRMs indicated transplant rejection with negative biopsy results (reason for less than one hundred percent (100%) specificity), all of these patients went on to have transplant rejection within twenty-four (24) to forty-eight (48) hours.

However, simple IMEG amplitude measurement is subject to variation due to the patient's daily rhythm, exercise status, and medications. A drop in amplitude may not always correlate to a rejection reaction. Moreover, because conventional UPPRMs provide at best only periodic monitoring (i.e., only while the patient is sleeping) the IMEG data registered by the UPPRMs does not provide the best data for determining a rejection reaction.

SUMMARY OF THE INVENTION

These and other shortcomings are addressed by the present invention, which according to one embodiment provides a method of monitoring a transplanted heart including the steps of: (a) during a first data collection session occurring at a reference time, registering an electrical signal from a patient's heart, the electrical signal configured as a first series of waveforms; (b) generating from the first series of waveforms, a reference waveform representative of the average characteristics of the waveforms collected during the first data collection session; (c) during a subsequent data session occurring at a time subsequent to the reference time, registering an electrical signal from a patient's heart, the electrical signal configured as a second series of waveforms; (d) generating from the second series of waveforms, a registered waveform representative of the average characteristics of the waveforms collected during the second data collection session; and (e) comparing the registered waveform to the reference waveform to determine whether the heart is functioning properly.

According to another aspect of the invention, a method of monitoring a transplanted heart includes the steps of: (a) during a data collection session, registering an electrical signal from a patient's heart, the electrical signal configured as a series of waveforms; (b) evaluating whether each of the waveforms is usable according to a predetermined standard; (c) discarding waveforms which are not usable; (d) storing the remaining waveforms in a database for evaluation; and (e) comparing the stored waveforms to a reference waveform to determine whether the heart is functioning properly.

According to another aspect of the invention, a method of processing data for monitoring a patient's heart includes the steps of: (a) during a data collection session, registering an electrical signal from a patient's heart, the electrical signal configured as a series of waveforms, wherein each of said waveforms represents a QRS complex of a myocardial electrogram including at least one upslope element extending to a peak; (b) establishing a minimum slope value; (c) comparing the actual slope value of each portion of the waveform to the minimum slope value; and (c) designating any point within the waveform in which the actual slope value is less than the minimum slope value to be a peak.

According to another aspect of the invention, a system for monitoring a patient's heart includes: (a) a registering unit structured to be implanted into the patient's body, the registering unit adapted to be connected in electrical communication with the patient's heart and to register an electrical signal from the patient's heart; and (b) a local data unit in operable communication with the registering unit and adapted to receive data corresponding to the registered electrical signal, the local data unit adapted to transmit data over a remote communications link to a computer.

BRIEF DESCRIPTION OF THE DRAWINGS

The invention may be best understood by reference to the following description taken in conjunction with the accompanying drawing figures in which:

FIG. 18 is a table depicting a scale of rejection.

DETAILED DESCRIPTION

Figure 1:
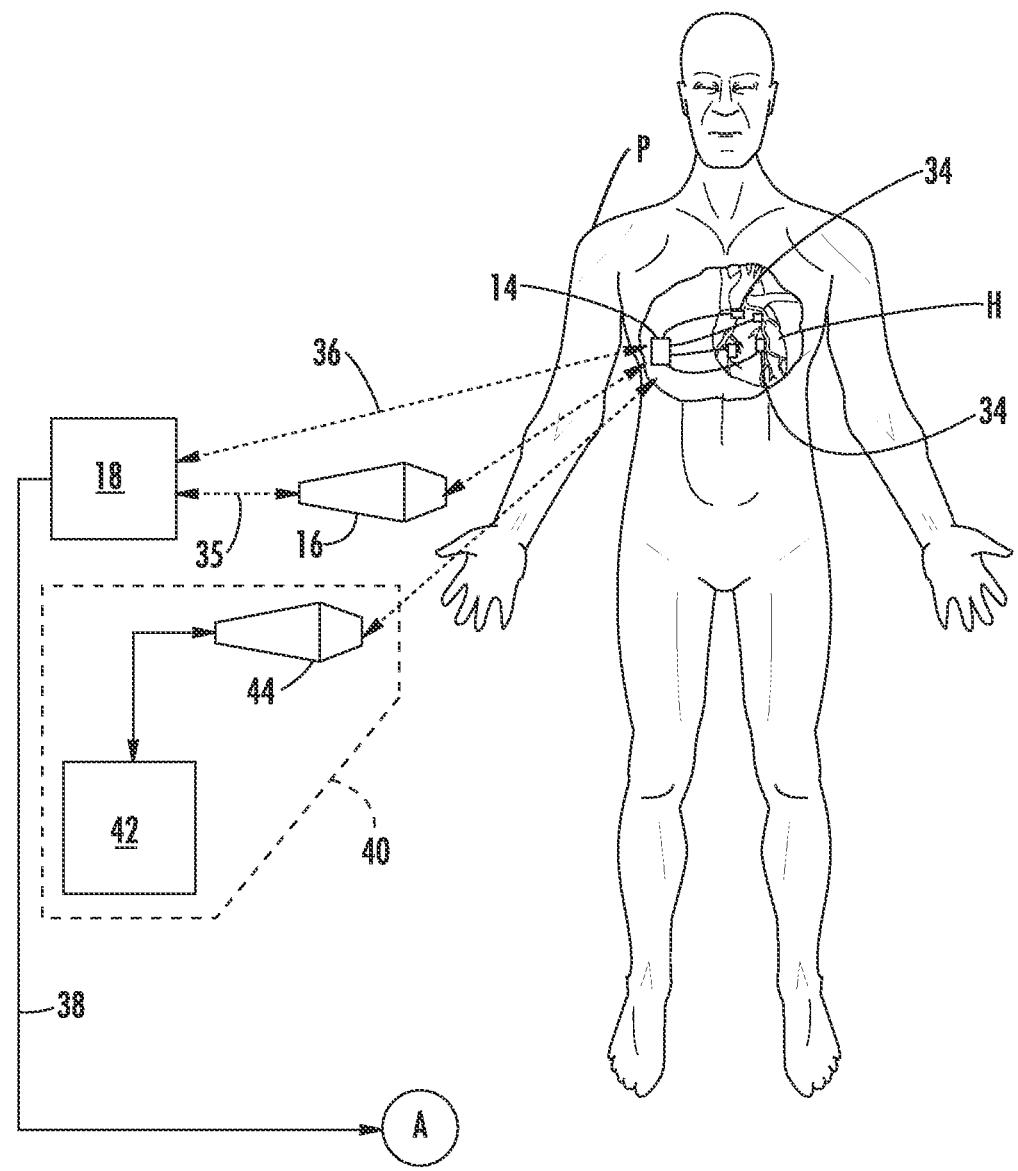
FIG. 1 is a diagram illustrating a system for monitoring a patient's heart, according to one aspect of the present invention.
Figure 2:
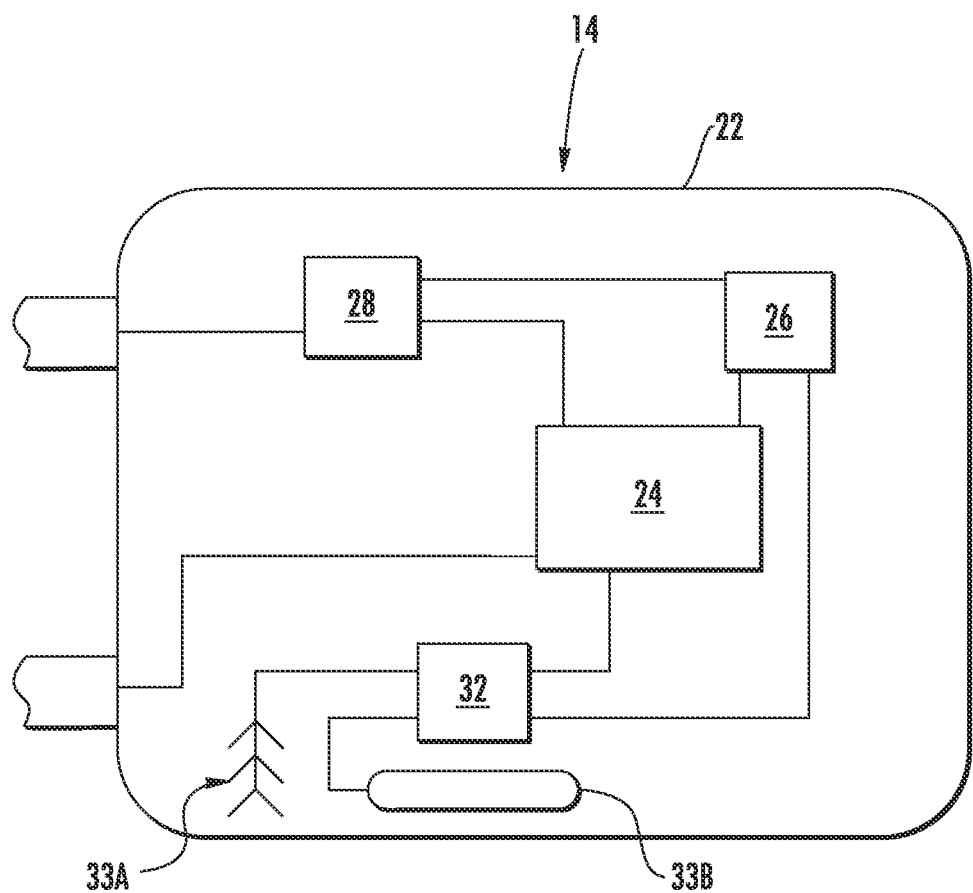
FIG. 2 is a block diagram illustrating a registering unit, according to one embodiment of the present invention.
Figure 3:
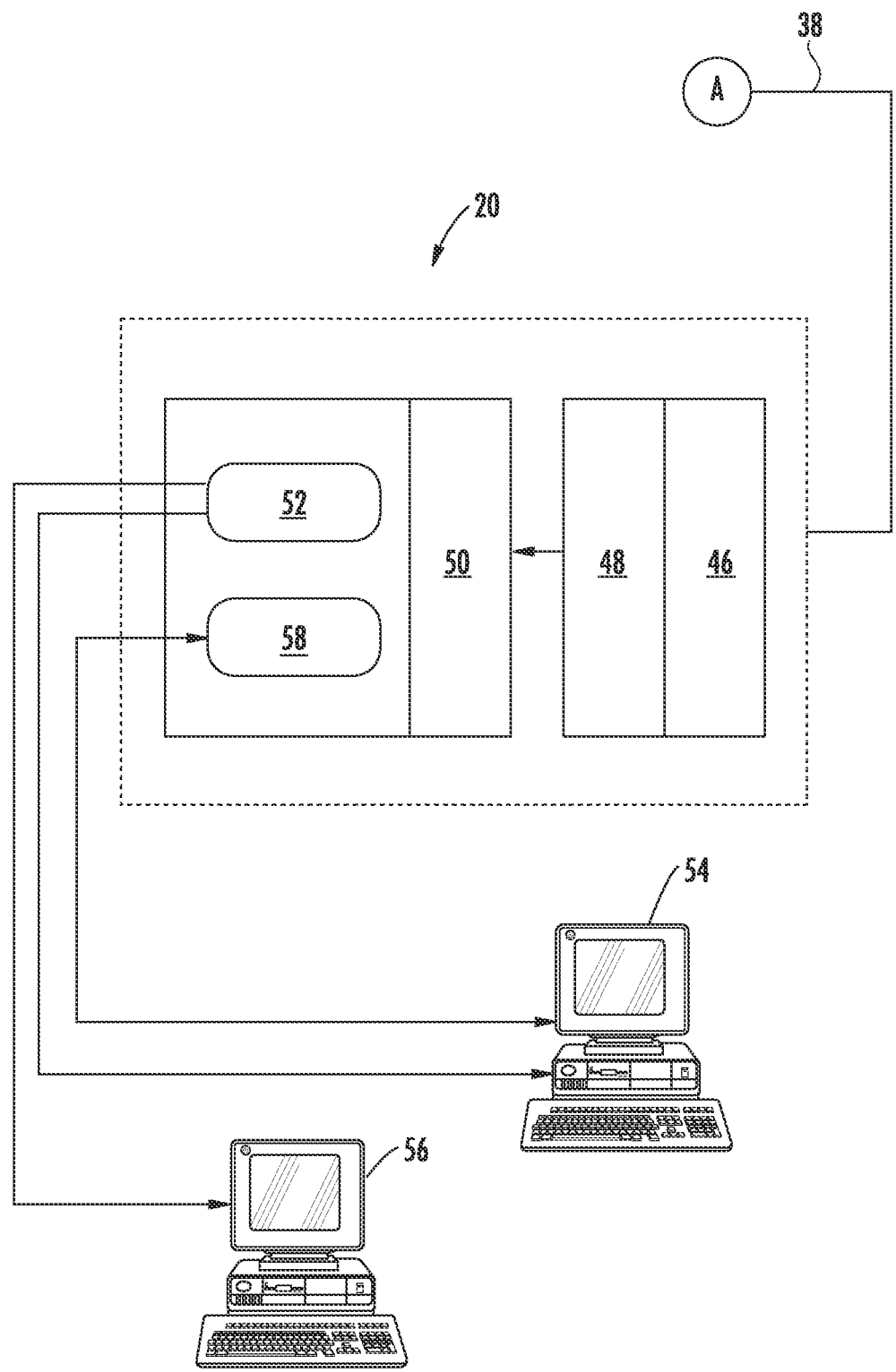
FIG. 3 is a block diagram showing a portion of the monitoring system of FIG. 1.

Referring to the drawings wherein identical reference numerals denote the same elements throughout the various views, FIGS. 1-3 illustrate a system for monitoring the heart "H" of a heart transplant patient or a patient suffering congestive heart failure or other cardiac ailment. The system includes an implantable registering unit 14 for non-invasive monitoring of a patient's heart H, an optional relay unit 16 for interrogating the registering unit, a local data unit 18, and a data server 20.

The registering unit 14 is structured to be implanted into the patient's body "P" and, thus, preferably includes a housing 22 constructed of a relatively rigid material that is biologically inert, such as titanium or silicone. Any commercially available pacemaker with appropriate software modifications may be used as the registering unit 14. As illustrated in FIG. 2, the registering unit 14 includes a controller 24, such as a microprocessor operating under software control or a programmable logic controller (PLC), an energy source 26 (e.g. a storage battery), a transceiver 32, and a transducer. The registering unit 14 can optionally include a signal generator 28 structured to provide electrical stimulus to the patient's heart, a therapeutic process commonly referred to as "pacing." The use of electrical stimuli to treat disorders such as bradyarrhythmias, or slow heart rhythms, and tachyarrhythmias, or fast heart rhythms, is well known to those skilled in the art and will not be further described herein. The energy source 26 is structured to provide electrical or thermal energy to the other components of the registering unit 14. The transceiver 32 and transducer are configured to communicate with a compatible transducer (not shown) in the relay unit 16 or other external device. Such communication may be through radio frequency (RF), in which case the transducer (generally referred to as 33) would be a conventional antenna, shown at 33A, or through inductive coupling, in which case the transducer would be an induction coil, shown at 33B. If an inductive coupling is provided, either as part of the transducer 33 or separately, it may also be used to provide power to the registering unit 14 or to recharge the energy source 22, or both.

The controller 24 communicates electrically with the patient's heart H via one or more sets or pairs of electrodes 34. In the illustrated example, the system includes two pairs of electrodes 34. The electrodes 34 can comprise any one of a number of commercially available epicardial (outside the surface of the heart) or endocardial (inside the heart) electrodes. Example of suitable electrodes 34 include screw-in epicardial bipolar IS I leads, or suture-on leads. The electrodes 34 preferably are attached to the heart H at the left and right ventricles, and left and right atriums. The electrodes 34 can be positioned at other areas about the patient's heart H, depending on a variety of factors including, but not limited to, whether the patient is a heart transplant patient or suffering from congestive heart failure, the physical characteristics of the patients heart, or need for cardiac pacing. The electrodes 34 can be modified to include pressure sensors, which gauge vigor or degree of myocardial contraction.

The local data unit 18 is used to receive, store, and optionally process data from the registering unit 14. The local data unit 18 can include a computer, microprocessor, or central processing unit operating under software control, with an associated data repository comprising, for example, flash memory, RAM, EEPROM, hard disk, floppy disks, CD or DVD-ROM, etc., and a transceiver or other data communication means (e.g. a TCP/IP network adapter or modem).

The local data unit 18 is placed in communication with the registering unit 14, for example using a relay unit 16, such as the illustrated handheld wand. The relay unit 16 is configured to receive data from the registering unit 14 and transfer it to the local data unit 18, and to receive instructions transmitted by the local data unit 18 and transmit those instructions to the controller 24 of the registering unit 14 via the transducer 33. The relay unit 16 includes a transducer (such as an induction coil), power source, data storage means, and transceiver compatible with the with that of the registering unit 14. In use, the relay unit 16 exchanges data bidirectionally with the registering unit 14, for example by inductive coupling at short range or by RF. The data is then either stored for later transfer to the local data unit 18, or immediately transferred to the local data unit 18. The transfer between the local data unit 18 and the relay unit 16 occurs through a communications link 35 such as a cable, infrared transmitter, or wireless link (e.g. BLUETOOTH wireless protocol). Optionally, the local data unit 18 may communicate directly with the registering unit 14 through a radio frequency (RF) communications link, shown schematically at 36.

Upon receipt of instructions from the relay unit 16 or the local data unit 18, the registering unit 14 begins monitoring and transmits data (either through the relay unit 16 or via the communications link 36). The local data unit 18 receives data from the registering unit 14 and then transfers that data over a remote communications path 38 such as a wireless or wired packet-switched network (e.g. a local area network, a wide area network, or Internet), over telephone lines using a modem, or through satellite connection. The remote communications path 38 may be encrypted for security purposes. The data is then received by the data server 20 at a remote location (see FIG. 3). Optionally, the data may be received from the registering unit 14 and then stored by the local data unit 18 for later transmission to the data server 20.

The local data unit 18 may be located at the same location as the relay unit 16 and the patient, such as at a medical care facility or office or at the patient's home. For example, the relay unit 16 can be connected in operable communication with the local data unit 18 through a serial port connection or through a USB connection. The local data unit 18 could also be disposed remotely from the relay unit 16 and the patient. According to this construction, the relay unit 16 would be placed in operable communication with the local data unit 18 via a computer network, including, but not limited to, the Internet, a local area network, a wide area network, a wireless network (such as satellite), a dial-up modem, etc., so that the relay unit 16 can communicate with the local data unit 18.

A physician interface unit 40 may also be provided. This comprises a computer 42 (e.g. a laptop microcomputer) and a relay unit 44 similar to the relay unit 16 described above, or other suitable communications link compatible with the registering unit 14. The physician interface unit 40 is programmed with software enabling it to receive data from the registering unit 14 and display the data for review, for example to show graphically in real time the data measured and transmitted by the registering unit 14. It may also be programmed to perform the data analysis described below. The physician interface unit 40 is also able to send instructions to the registering unit 14 through the relay unit 44, for example to change the value of programmable parameters of the registering unit 14 (such as a measurement interval), to interrogate the registering unit 14 for the actual values of the programmable parameters, or to command the registering unit 14 to transmit data or to begin or end pacing.

FIG. 3 illustrates the data server 20 and related components. The data server 20 receives data from the local data unit 18 through the remote communications path 38 described above. A data receiving software module 46 may be provided for this purpose. The data may then processed by an analysis software module 48 which is capable of performing calculations, reference-waveform comparisons, and/or signal analysis described below. The processed data is stored in a database 50, such as a structured query language (SQL) database. The data may then be accessed by an electronic medical records (EMR) software module 52 which permits a user to view summaries of patient data, graphical analysis screens, and the like. The EMR software module 52 may be accessed by a monitoring service at a remote computer 54 (e.g. over a secure network connection), or by another authorized user, such as a patient's primary care physician, again at a remote computer 56 which communicates with the data server 20 by a network connection. A billing software module 58 may also be provided within the data server 20 to track usage by the monitoring service or other authorized user.

When monitoring a patient's heart H, the registering unit 14 will be instructed, using either the communications link 36 or the relay unit 16, to initiate monitoring of the patient's heart. The controller 24 begins registering or sensing the electrical signals emitted by the patient's heart. Data corresponding to the registered electrical signals is communicated to the transceiver 32, which then communicates the data to the local data unit 18 through the relay unit 16 or through the communications link 36.

Figure 4:
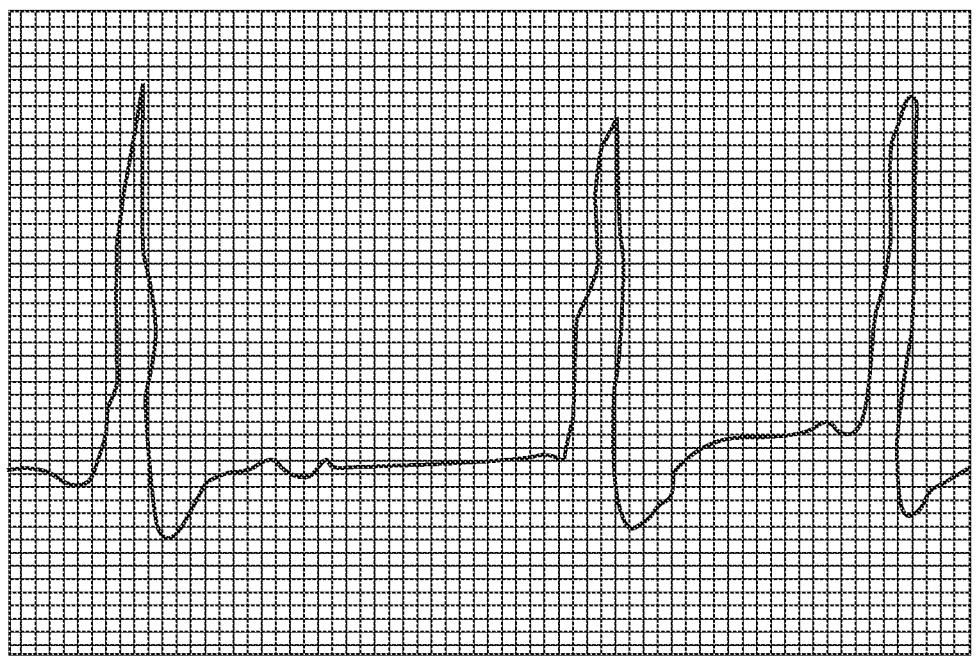
FIG. 4 is a diagram showing a digitized electrogram or waveform, according to one aspect of the present invention.

Analysis software, for example running on either the local data unit 18 or the data server 20, allows precise discrimination of intracellular and extracellular myocardial dynamics, as well as volume changes and myocardial strength of contraction in the patient's heart H. The analysis software is structured to analyze the data received from the patient's heart H in several ways. According to one procedure, each time data is received corresponding to the electrical signals received by the registering unit 14 from the patient's heart H, the analysis software digitally creates or generates a graphic representation of a patient's intracardiac electrogram, such as the one illustrated in FIG. 4. In accordance with conventional practice, the horizontal axis of this graphic represents a time scale (e.g. seconds), and the vertical axis of the graphic represents amplitude (e.g. Volts or millivolts). For example, the electrical signals received from the patient's heart may comprise analog electrogram signals that are digitized at 1 KHz with a 8-bit resolution. Preferably, a "baseline" or reference electrical signal is registered using the above-referenced procedure to produce a reference waveform that is stored for later analysis. The reference electrical signal can be obtained when the patient undergoes heart transplant, when the registering unit 14 is implanted, or at some other predetermined time.

Additionally, the registering unit 14 has the ability to measure resistance to current flow (impedance) from pacing stimuli given to the myocardium. The impedance is represented as a value in Ohms and is received in the data provided from the device. Multiple sets of data (unipolar & bipolar for each lead) will be received per data transmission. The impendence data is separate from the electrogram data.

Several techniques may be used to generate the waveforms or portions thereof so as to produce data which is "cleaner" than the raw digitized data, i.e. relatively free from effects of electrical noise or digitization errors, and easier to analyze.

For example, The QRS complex of the electrogram may be analyzed without the P-wave and S-wave segments. The Q-wave segment may be included in the analysis if it is present and sufficiently identifiable. Within the QRS complex, the waveform comprises a series of line segments or portions having a high slope or first derivative, such that peaks (and nadirs) occur as sharply delineated events (i.e. the curves are strongly convex). Accordingly, peak detection (or nadir detection) may be implemented by establishing a minimum slope value. To accomplish this, the entire QRS complex is evaluated, either by the analysis software or by separate pre-processing software, for the presence of any location where the absolute value of the slope is less than the minimum value. Each of these locations are identified as a peak (or a nadir). An example of a suitable threshold value is 0.5 mV/s.

The QRS complexes in the waveforms appear as deviations from a baseline or generally horizontal trace, which may or may not be equal to a zero electrical potential line. The value (i.e. voltage level) of the baseline affects other measurements such as baseline-to-peak amplitude and area under the curve (described in more detail below). The specific value of the baseline is calculated based on the specific equipment configuration.

Figure 16:
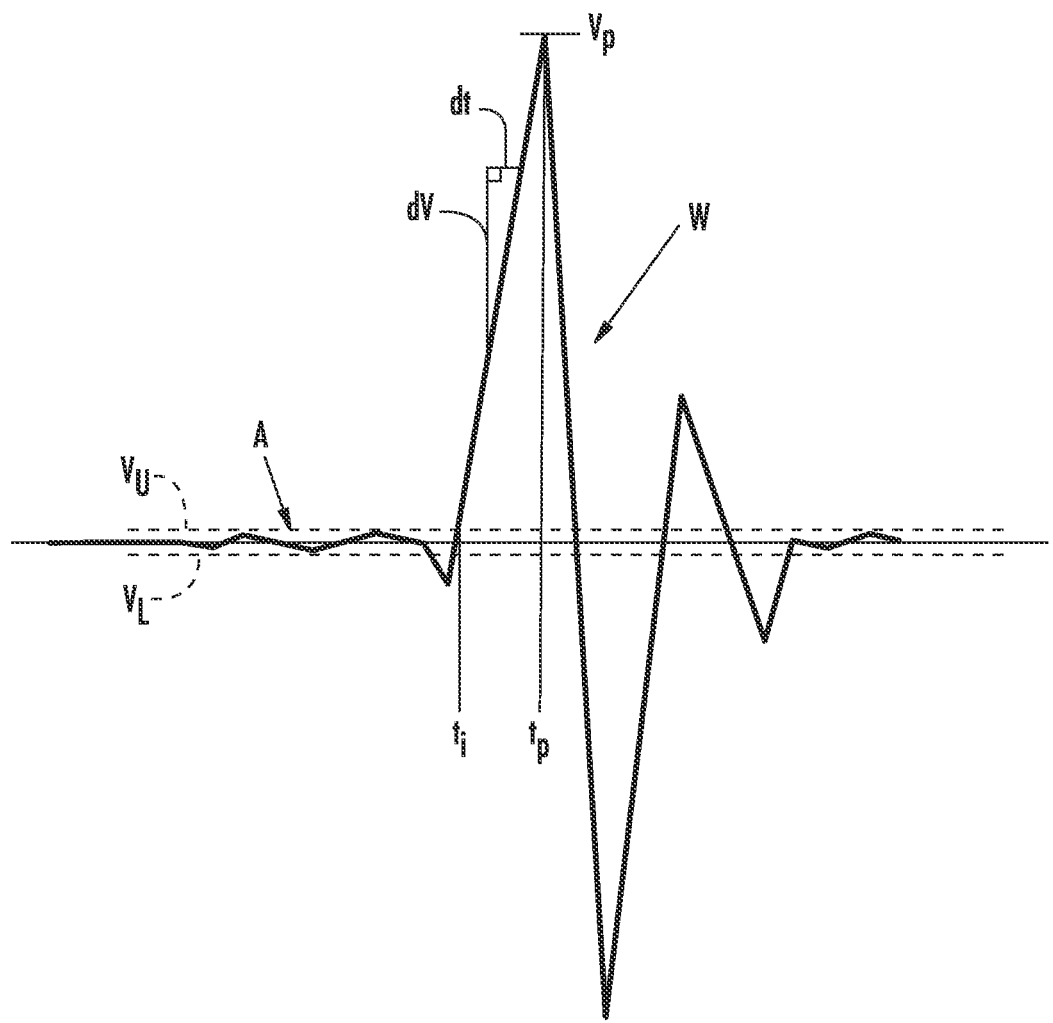
FIG. 16 is a diagram illustrating an exemplary electrogram with a hysteresis band applied thereto.

In practical application, portions of the waveform ahead and behind of the QRS complex will not match the established baseline, i.e. they will not be simple horizontal traces, but will rather exhibit many small deviations. This is depicted by arrow "A" of the exemplary waveform "W" in FIG. 16. In order to reduce the uncertainty in several measurements caused by this variation, a deadband or hysteresis band with preselected upper and lower voltage limits "$V_U$" and "$V_L$" may be applied to the waveform W. For purposes of analysis, the beginning (or end) of the QRS complex is assumed to begin or end at the time value $t_i$ which the upslope or downslope of the waveform W intercepts the relevant limit $V_U$ or $V_L$.

One manner in which the hysteresis band intercept may be accurately located is to apply a linear slope calculation to the relevant portion of the waveform W. For example, using the peak detection method described above, the time $t_p$ at which the dominant peak occurs and the peak voltage $V_p$ will be known. The slope dv/dt of the immediately preceding segment is then determined, by calculating a linear ratio using an appropriate dt (e.g. 1 ms if a 1-kHz sampling rate is being used). Once the slope is known, it may be extrapolated back to calculate the intercept time $t_i$, for example using equation (1) below. The resulting time $t_i$ is taken to the be the "beginning" of the upslope. A similar procedure may be used to determine the intercept of other upslopes or downslopes within the waveform W.

$$t_i = t_p - (v_p - v_u)(dv/dt)^{-1} \quad (1)$$

Identification of the R-wave and the S-wave of the QRS complex may be enhanced by implementing known relationships therebetween. Specifically, the amplitudes of the R-wave and S-wave are inversely related to each other, the S-wave always follows the R-wave in time sequence, and the R-wave is always the first positive peak in the QRS complex. When a combination of these features are observed, a positive identification of the R-wave and S-wave is made.

Figure 17:
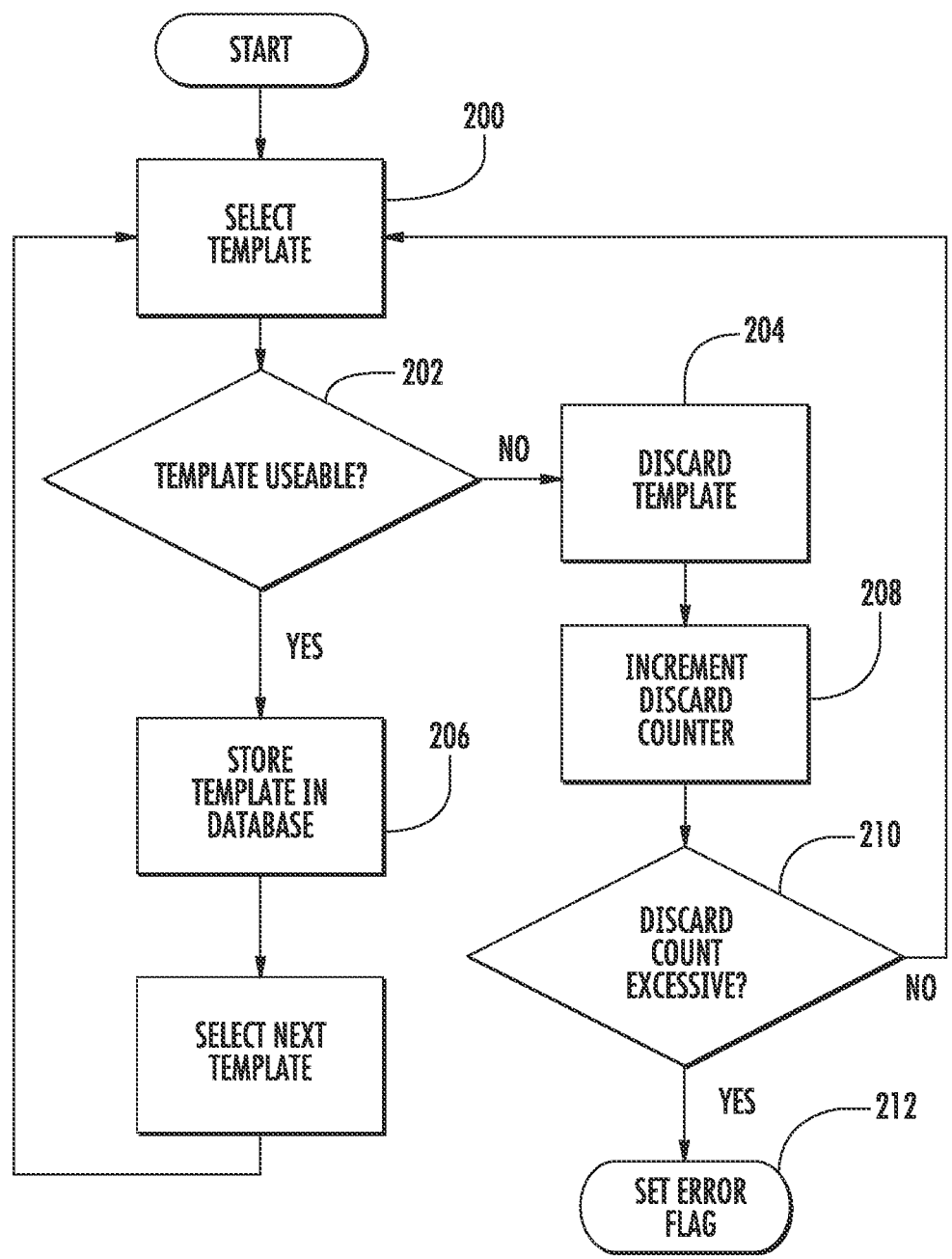
FIG. 17 is a block diagram showing a data processing flow in accordance with an aspect of the present invention.

The preprocessed data is evaluated as follows, with reference to FIG. 17. First, a waveform resulting from a data collection session is selected (block 200) to be observed and evaluated against a predetermined standard in block 202. This process can occur in real-time as the waveforms are collected, or it may be applied to a set of waveforms which have been temporarily stored. If the waveform does not meet the applicable standard it is deemed "not usable". It is discarded (block 204) and not used in the generation of the averaged waveform, as described below. The purpose of this initial step is to serve as a gross check on the quality of the data and to prevent outlying data from corrupting the data population, possible leading to incorrect diagnosis. If the waveform is usable, it is stored in a statistical database (block 206), or marked for permanent storage.

Various techniques may be used to implement this step. For example, the peak-to-peak distance of each QRS complex may be calculated. If any one QRS complex has a peak-to-peak distance varying from the average peak-to-peak distance by more than a selected threshold value, for example plus or minus 5%, then that entire QRS complex would be discarded and not used in the generation of the averaged waveform, as described below.

As the data is initially tested, a counter is incremented (block 208) each time a waveform is discarded. A high value of this counter could indicate an equipment fault or human error in collecting the data. High values may also indicate extreme acute rejection. Accordingly, this counter serves as a gross check for allograft rejection. If the counter exceeds a predetermined standard at block 210, the process is stopped and an error flag is set for operator attention at block 212. The process is repeated until all of the waveforms in the data collection session have been evaluated.

Next, the remaining waveforms from the data collection session are used to construct a single average waveform. The initial waveform generated at the reference time, immediately or very shortly after transplantation, becomes the reference waveform described above. Each subsequent data collection session results in a new averaged registered waveform. For example, a data collection session may be conducted three times each day after transplantation, resulting in three new registered waveforms each day.

When creating a representative waveform, the "average" image may be created in two different ways. In a first exemplary technique, all of the non-discarded QRS complexes recorded are averaged together to generate a single average waveform.

In another exemplary technique, the individual elements described above are identified for each non-discarded QRS complex in the data population. Those individual elements are averaged together, resulting in an average Q-wave, R-wave, S-wave, etc. Then the individually-averaged elements are assembled to form a composite waveform.

Various portions, features, or elements of the waveforms can be used as a basis for comparison between the reference waveform and the registered waveform(s) in determining the presence or absence of rejection.

Figure 8:
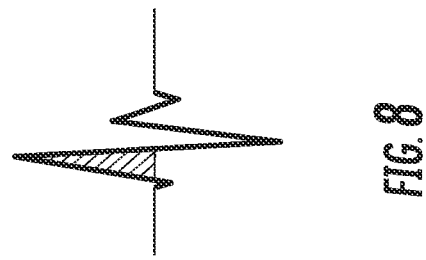
FIG. 8 is a diagram illustrating the measurement of the area under the major peak of an electrogram.
Figure 7:
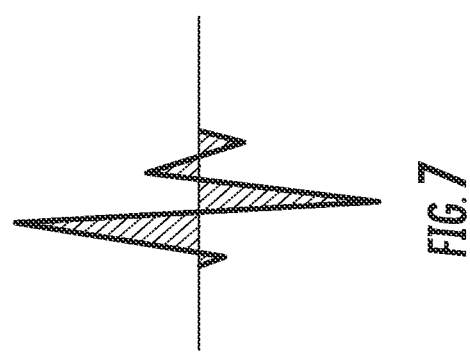
FIG. 7 is a diagram illustrating the measurement of the total area under the peaks of an electrogram.
Figure 9:
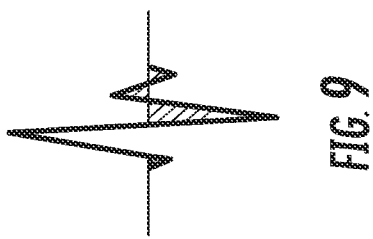
FIG. 9 is a diagram illustrating the measurement of the total area under the minor peaks of an electrogram.

One element is area measurement, several possible variations of which are shown in FIGS. 7 through 9, in which the area being measured in shaded for identification. In FIG. 7, the total area inscribed under the curves of the QRS complex is measured. In FIG. 8, only the area inscribed under the dominant peak is measured. In FIG. 9, the area inscribed under all of the minor peaks is measured. Known techniques of numerical integration are used to implement these area measurements.

Figure 10:
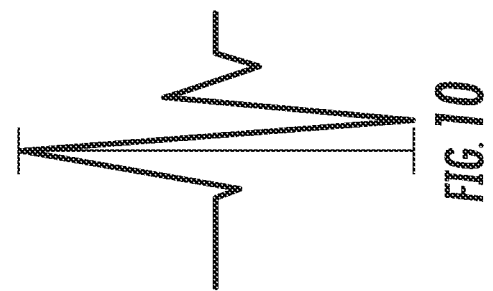
FIG. 10 is a diagram illustrating the measurement of the peak-to-peak amplitude of an electrogram.
Figure 11:
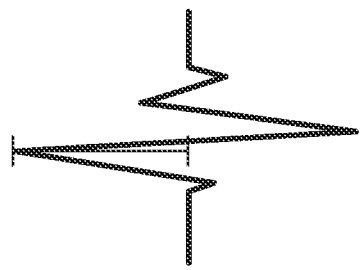
FIG. 11 is a diagram illustrating the measurement of the baseline-to-peak amplitude of an electrogram.

Another element is amplitude measurement. For example, FIG. 10 illustrates peak to peak amplitude measurement, while FIG. 11 illustrates baseline to dominant peak amplitude measurement. These values are measured in millivolts (mV).

Figure 12:
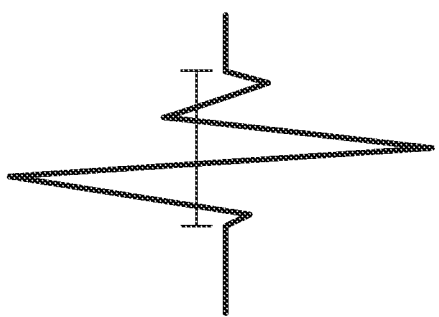
FIG. 12 is a diagram illustrating the measurement of the total duration of an electrogram.

Another element is duration. FIG. 12 illustrates the measurement of total electrogram duration (i.e. baseline-to-baseline). The total electrogram duration is measured in milliseconds (ms).

Figure 13:
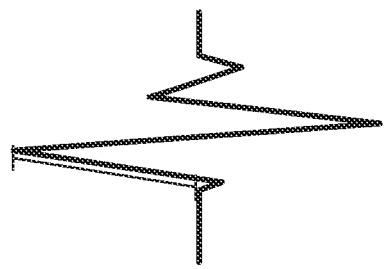
FIG. 13 is a diagram illustrating the measurement of the slope of the leading edge of the R-wave of an electrogram.
Figure 14:
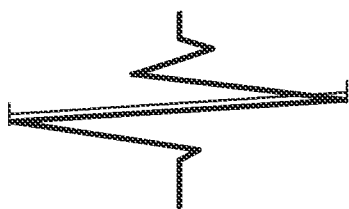
FIG. 14 is a diagram illustrating the measurement of the slope of the major-peak-to-nadir downslope of the R-wave of an electrogram.

Another element is slew rate or slope. FIG. 13 illustrates the measurement of the dominant peak upslope, while FIG. 14 shows measurement of the dominant peak to nadir downslope. The slew rates are measured in millivolts per second (mV/s).

Figure 15:
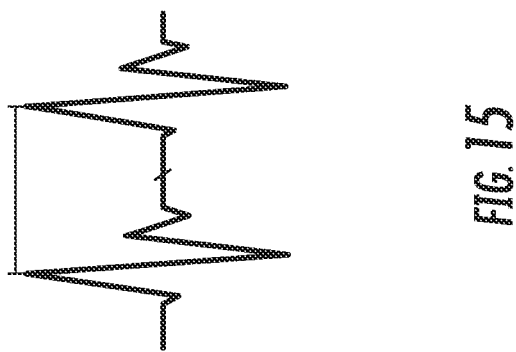
FIG. 15 is a diagram illustrating the measurement of the interval between R-wave peaks of successive electrograms.

In addition to the measurements described above, there are additional measurements which may or may not be valuable in predicting heart transplant rejection, but are valuable for other diagnostic purposes, and the data needed to compute the results is available from the implanted registering unit 14. Example of such additional measurements include:

R-to-R interval: Using time and the dominant peak points the average amount of time between R-waves can be calculated for the multiple electrograms recorded. The R-to-R interval (shown in FIG. 15) is measured in milliseconds.

Current heart rate and variability: heart rate is measured in beats per minute (bpm). Heart rate variability may be calculated by analyzing the time series of beat-to-beat intervals. The amount of time between beats will be calculated to determine variability over multiple sessions of data.

Data evaluation and comparison of the registered waveforms to the reference waveform may be carried out in various ways by the analysis software. One method of comparison involves quantifying the differences between a selected one of the registered waveforms and the reference waveform.

Figure 5:
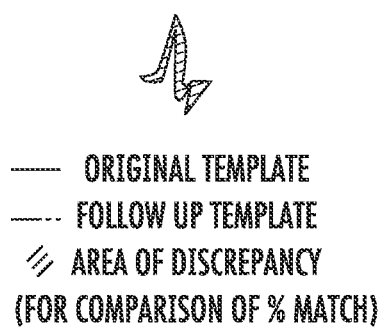
FIG. 5 is a diagram graphically illustrating a comparison of a first waveform, which corresponds to a registered electrical signal from a patient's heart, to a second waveform, which corresponds to a reference electrical signal from the patient's heart, according to one aspect of the present invention.
Figure 6:
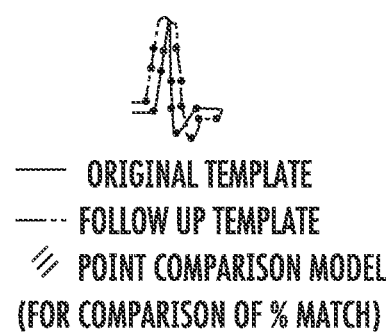
FIG. 6 is a diagram graphically illustrating a comparison of a first waveform, which corresponds to a registered electrical signal from a patient's heart, to a second waveform, which corresponds to a reference electrical signal from the patient's heart, according to one aspect of the present invention.

Using this method, the difference in one or more of the individual signal elements or measurements described above (e.g. area, amplitude, slew, or impedance) between the reference waveform and the registered waveform is measured and used to assess heart function. The waveforms may also compared by measuring the total area of discrepancy between the waveforms and determining a comparison percentage match, as shown in FIG. 5, or by a point-to-point comparison, as shown in FIG. 6.

Alternatively, evaluation of the waveforms may be carried out based on a multivariable statistical analysis of shifts in the registered data. When the average registered waveforms are created, each new waveform, along with the values of all of its individual elements, becomes a member of a statistical population in a database. As rejection takes place, causing changes in the heart H, it is expected that the individual waveform elements described above will change in different ways. For example, the R-wave upslope might increase while the peak-to-peak amplitude decreases. No one of these elements necessarily represents a simple rejection-specific parameter, rather the aggregate difference, or certain combinations of changes, represents allograft rejection. However, the aggregate effect of these changes can be correlated to the presence of rejection.

Under either of the methods described above, a scale of rejection can be created. The greater the deviation from a nominal condition (determined either statistically or in terms of a scalar measurement), the more likely actual rejection is taking place, or the greater the severity of rejection. FIG. 18 illustrates an example of a possible scale of rejection, with numerical values ranging from 0 to 7. Each increasing number on the scale is indicative of greater deviation of the registered waveform data from the reference waveform. The numbers on the scale may be likened to "grades" of rejection.

It is also possible correlate the scale of rejection to clinical results (from biopsies, autopsies, etc.) and to established "grades" of myocardial allograft rejection. For illustrative purposes only, the scale of rejection is shown as being correlated to established prior art "grades" for cardiac biopsy, e.g. 0, 1, 1A, 1B, 2, 3, 3A, 3B, 4.It is noted that the first degree on the scale of rejection correlates to a biopsy grade of "0". This is because the method described herein is able to detect very slight changes in the recorded data. As such, it is believed that changes in the heart H measurable on the scale of rejection will be present even if no rejection is yet observable in a contemporaneous biopsy. This can occur because the method described herein is sensitive to changes throughout the structure of the heart, while a biopsy may show negative results if it is not taken from a localized area that happens to site where rejection is just starting. The present method thus has the possibility of detecting rejection early enough so as to be "predictive" in nature when compared to biopsies. Early detection of rejection advantageously permits prompt initiation of life saving therapy. This early detection is especially important in immuno-compromised patients who are prone to rapid onset of acute rejection.

The figures and text herein describe methods and systems according to various aspects of the invention. It will be understood that each step described herein can be implemented by computer program instructions. These computer program instructions may be loaded onto a computer or other programmable apparatus to produce a machine, such that the instructions which execute on the computer or other programmable apparatus create means or devices for implementing the described functions or step(s). These computer program instructions may also be stored in a computer-readable memory that can direct a computer or other programmable apparatus to function in a particular manner, such that the instructions stored in the computer-readable memory produce an article of manufacture, including instruction means or devices which implement the specified functions or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the specified functions or step(s).

It will also be understood that each step or combinations of steps described herein can be implemented by special purpose hardware-based computer systems which perform the specified functions or steps, or combinations of special purpose hardware and computer instructions.

The foregoing has described systems and methods for monitoring a patient's heart. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation, the invention being defined by the claims.

What is claimed is:

1. A method of monitoring a transplanted heart, comprising:
   (a) during a first data collection session occurring at a reference time, registering an electrical signal from a patient's heart, the electrical signal configured as a first series of waveforms emitted by the patient's heart that is not in response to an electrical stimulus;
   (b) generating from the first series of waveforms, a reference waveform representative of the average characteristics of the waveforms collected during the first data collection session;
   (c) during a subsequent data collection session occurring at a time subsequent to the reference time, registering an electrical signal from a patient's heart, the electrical signal configured as a second series of waveforms emitted by the patient's heart that is not in response to an electrical stimulus;
   (d) generating from the second series of waveforms, a registered waveform representative of the average characteristics of the waveforms collected during the subsequent data collection session; and
   (e) comparing the registered waveform to the reference waveform to determine whether the heart is functioning properly.

2. The method of claim 1 in which step (e) is carried out by:
   (a) measuring the difference between at least one element of the registered waveform and a corresponding element of the reference waveform; and
   (b) characterizing the difference in a scale of rejection in which a greater degree of difference corresponds to a greater degree of allograft rejection.

3. The method of claim 1 further comprising repeating steps (c)-(d) at selected intervals after the reference time so as to generate a plurality of registered waveforms.

4. The method of claim 3 in which step (e) is carried out by:
   (a) adding the plurality of registered waveforms to a statistical database to create a data population;
   (b) determining at least one difference between the registered waveforms and the reference waveform based on a statistical analysis of a plurality of elements of the registered waveforms and corresponding elements of the reference waveform; and
   (c) characterizing the difference in a scale of rejection in which a greater degree of difference corresponds to a greater degree of allograft rejection.

5. The method of claim 1 further comprising:
   (f) prior to step (b), evaluating whether each of the waveforms in the first series is usable according to a predetermined standard;
   (g) discarding waveforms from the first series which are not usable; and (h) storing the remaining waveforms of the first series in a database for use in generating the reference waveform.

6. The method of claim 5 further comprising: (i) incrementing a discard counter each time a waveform is discarded; (j) comparing the value of the discard counter to a predetermined limit; and (k) setting an error flag if the discard counter exceeds a predetermined limit.

7. The method of claim 1 further comprising:
(f) prior to step (d), evaluating whether each of the waveforms in the subsequent series is usable according to a predetermined standard;
(g) discarding waveforms from the subsequent series which are not usable; and
(h) storing the remaining waveforms of the subsequent series in a database for use in generating the registered waveform.

8. The method of claim 7 further comprising: (i) incrementing a discard counter each time a waveform is discarded; (j) comparing the value of the discard counter to a predetermined limit; and (k) setting an error flag if the discard counter exceeds a predetermined limit.

9. The method of claim 1 wherein the reference time is when the heart is transplanted into the patient.

10. A method of claim 1, wherein each of said waveforms represents a QRS complex of a myocardial electrogram including at least one upslope element extending to a peak, and wherein the method further comprises:
(f) establishing a minimum slope value;
(g) comparing the actual slope value of each portion of the upslope to the minimum slope value; and
(h) designating any point within the waveform in which the actual slope value is less than the minimum slope value to be a peak.

11. The method of claim 10 further comprising:
(i) establishing the time value at which the peak occurs;
(j) applying a hysteresis band with predetermined upper and lower voltage limits to the waveform of the QRS complex;
(k) calculating a voltage-time slope for a segment of the upslope immediately preceding the peak;
(l) using the calculated voltage-time slope, linearly extrapolating the upslope to a point at which a voltage value thereof intercepts the upper limit of the hysteresis band; and
(m) establishing the time value at which the interception occurs.

12. The method of claim 1 wherein the reference and registered electrical signal are QRS complexes of an intracardiac electrogram, or portions thereof.

13. A method of monitoring a transplanted heart, comprising:
(a) registering a first electrical signal from a patient's heart, the first electrical signal configured as a first series of waveforms comprising at least a portion of a QRS complex of an intracardiac electrogram;
(b) generating from the first series of waveforms, a reference waveform representative of the average characteristics of the waveforms;
(c) registering a second electrical signal from a patient's heart subsequent to registering the first electrical signal, the second electrical signal configured as a second series of waveforms comprising at least a portion of a QRS complex of an intracardiac electrogram;
(d) generating from the second series of waveforms, a registered waveform representative of the average characteristics of the waveforms; and
(e) measuring the difference between at least one element of the registered waveform and a corresponding element of the reference waveform; and
(f) characterizing the difference in a scale of rejection in which a greater degree of difference corresponds to a greater degree of allograft rejection.

14. The method of claim 13 wherein the first and second electrical signals are emitted by the patient's heart and not in response to an electrical stimulus.

15. A method of monitoring a transplanted heart, comprising:
(a) during a first data collection session occurring at a reference time, wherein the reference time is when the heart is transplanted into the patient, registering an electrical signal from a patient's heart, the electrical signal configured as a first series of waveforms emitted by the patient's heart that is not in response to an electrical stimulus;
(b) generating from the first series of waveforms, a reference waveform representative of the average characteristics of the waveforms collected during the first data collection session;
(c) during a subsequent data collection session occurring at a time subsequent to the reference time, registering an electrical signal from a patient's heart, the electrical signal configured as a second series of waveforms emitted by the patient's heart that is not in response to an electrical stimulus;
(d) generating from the second series of waveforms, a registered waveform representative of the average characteristics of the waveforms collected during the subsequent data collection session; and
(e) comparing the registered waveform to the reference waveform to determine whether the heart is functioning properly.

* * * * *